US009409972B2

(12) United States Patent
Uto et al.

(10) Patent No.: US 9,409,972 B2
(45) Date of Patent: *Aug. 9, 2016

(54) PHARMACEUTICAL COMPOSITION AND METHOD OF PREPARING SAME

(71) Applicants: SAISEI MIRAI CLINIC, Moriguchi-shi, Osaka (JP); TOKUSHIMA UNIVERSITY, Tokushima-shi, Tokushima (JP)

(72) Inventors: Yoshihiro Uto, Tokushima (JP); Hitoshi Hori, Tokushima (JP); Toshio Inui, Moriguchi (JP); Kentaro Kubo, Moriguchi (JP)

(73) Assignees: TOKUSHIMA UNIVERSITY, Tokushima-Shi (JP); SAISEI MIRAI CLINIC, Moriguchi-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/193,362

(22) Filed: Feb. 28, 2014

(65) Prior Publication Data

US 2014/0213522 A1    Jul. 31, 2014

Related U.S. Application Data

(63) Continuation of application No. 13/988,376, filed as application No. PCT/JP2012/072884 on Sep. 7, 2012, now Pat. No. 8,747,919.

(30) Foreign Application Priority Data

Sep. 14, 2011   (JP) ................................. 2011-200684

(51) Int. Cl.
| | |
|---|---|
| *A01N 65/00* | (2009.01) |
| *C07K 14/765* | (2006.01) |
| *A61K 35/16* | (2015.01) |
| *A61K 38/47* | (2006.01) |

(52) U.S. Cl.
CPC ............... *C07K 14/765* (2013.01); *A61K 35/16* (2013.01); *A61K 38/47* (2013.01)

(58) Field of Classification Search
CPC ...................................................... A61K 36/00
USPC ........................................................ 424/725
See application file for complete search history.

(56) References Cited

U.S. PATENT DOCUMENTS

2004/0224877 A1    11/2004   Pirie-Shepherd et al.

FOREIGN PATENT DOCUMENTS

| EP | 2612921 A1 | 7/2013 |
|---|---|---|
| JP | 5-97695 A | 4/1993 |
| JP | 6-99314 B2 | 12/1994 |
| WO | WO 2012/029954 A1 | 3/2012 |

OTHER PUBLICATIONS

Oberstein et al., Therap Adv Gastroenterol. Jul. 2013; 6(4): 321-337.*
International Preliminary Report on Patentability with Written Opinion, dated Mar. 16, 2014, for Application No. PCT/JP2012/072884 with English language translation.
Hori et al., "Drug discovery of dramatype-anticancer drugs base on oligosaccharide-processing of Gc protein (vitamin D-binding protein)," Radiation Biology Research Communications, vol. 39, No. 3, Sep. 29, 2004, pp. 328-341.
International Search Report issued in PCT/JP2012/072884, mailed on Oct. 23, 2012.
Uto et al., "B-Galactosidase Treatment is a Common First-stage Modification of the Three Major Subtypes of Gc Protein to GcMAF", Anticancer Research, vol. 32, 2012, pp. 2359-2364.
Uto et al., "Effect of the Gc-derived Macrophase-activating Factor Precursor (preGcMAF) on Phagocytic Activation of Mouse Peritoneal Macrophages", Anticancer Research, vol. 31, 2011, pp. 2489-2492.
Yamamoto et al., "Immunotherapy for Prostate Cancer with Gc Protein-Derived Macrophage-Activating Factor, GmMAF1", Translational Oncology, vol. 1, No. 2, Jul. 2008, pp. 65-72.
Yamamoto et al., "Immunotherapy of HIV-Infected Patients With Gc Protein-Derived Macrophage Activating Factor (GcMAF)," Journal of Medical Virology, vol. 81, No. 1, 2009, pp. 16-26.
Yamamoto et al., "Immunotherapy of metastatic breast cancer patients with vitamin D-binding protein-derived macrophage activating factor (GcMAF)", Int. J. Cancer, vol. 122, 2008, pp. 461-467.
Yamamoto et al., "Immunotherapy of metastatic colorectal cancer with vitamin D-binding protein-derived macrophage-activating factor, GcMAF", Cancer Immunol Immunother, vol. 57, 2008, pp. 1007-1016.
Yamamoto et al., "Role of Vitamin D3-Binding Protein in Activation of Mouse Macrophages," The Journal of Immunology, vol. 157, No. 4, Aug. 15, 1996, pp. 1744-1749.
Yamamoto et al., "Vitamin D3 binding protein (group-specific component) is a precursor for the macrophage-activating signal factor from lysophosphatidylcholine-treated lymphocytes," Proceedings of the Nat'l Academy of Sciences of the United States of America, vol. 88, No. 19, Oct. 1991, pp. 8539-8543.
Extended European Search Report dated Dec. 10, 2014 for European Application No. 12831559.5.

* cited by examiner

*Primary Examiner* — Michael Meller
(74) *Attorney, Agent, or Firm* — Birch, Stewart, Kolasch & Birch, LLP

(57) ABSTRACT

An object of the present invention is to provide a pharmaceutical composition comprising an enzyme-treated human serum which is useful for treatment and prevention of diseases such as a cancer and an infectious disease, and a method of preparing the same. The present invention relates to a method of preparing a pharmaceutical composition comprising an enzyme-treated human serum, comprising a step of bringing the human serum into contact with β-galactosidase and, to a pharmaceutical composition comprising an enzyme-treated human serum obtained by the preparation method.

1 Claim, 4 Drawing Sheets

PHARMACEUTICAL COMPOSITION AND METHOD OF PREPARING SAME

CROSS REFERENCE TO RELATED APPLICATIONS

This application is a Continuation of U.S. patent application Ser. No. 13/988,376 filed on May 20, 2013, which is the National Phase of PCT International Application No. PCT/JP2012/072884 filed on Sep. 7, 2012 and claims priority to Patent Application No. 2011-200684 filed in Japan on Sep. 14, 2011, all of which are hereby expressly incorporated by reference into the present application.

TECHNICAL FIELD

The present invention relates to a pharmaceutical composition comprising an enzyme-treated human serum which is useful for treatment and prevention of diseases such as a cancer and an infectious disease, and to a method of preparing the same.

BACKGROUND ART

Macrophage has a function of treating waste products in a human body and a defensive function against pathogens such as a microbe and a virus, and tumor cells. Macrophage also has a function as an effector of cell immunity via presentation of an antigen to T cell and production of interleukin 1. Accordingly, it is important to activate macrophage for treatment and prevention of a cancer and an infectious disease, and the activation of macrophage makes it possible to carry out treatment and prevention of a cancer and an infectious disease.

A factor for activating macrophage is, for example, an interferon, and its clinical application has been carried out. In addition, it is known that a certain kind of polysaccharides has an immunostimulating activity, and some of them are expected to be developed as an antiviral agent and an anticancer agent (Patent Document 1 or 2).

Further, a cancer advances via the steps of initiation (first stage, immortalization), promotion (second stage, growth) and progression (third stage, metastasis and invasion), and among these stages, it is the progression stage that has a relation to angiogenesis. Therefore, metastasis and invasion of a cancer can be suppressed by inhibiting the angiogenesis, and a medicament taking such an effect is useful as an inhibiting agent and a prophylactic agent for metastasis of a cancer.

PRIOR ART DOCUMENTS

Patent Documents

Patent Document 1: JP 05-097695 A
Patent Document 2: JP 06-099314 B

SUMMARY OF THE INVENTION

Problem to be Solved by the Invention

An object of the present invention is to provide a pharmaceutical composition comprising an enzyme-treated human serum which is useful for treatment and prevention of diseases such as a cancer and an infectious disease, and a method of preparing the same.

Means to Solve the Problem

The present inventors have made extensive studies and as a result, have found that when a human serum is subjected to enzyme treatment by bringing the human serum into contact with a specific enzyme, that is β-galactosidase or β-galactosidase and sialidase, the treated human serum shows excellent macrophage activating action and/or angiogenesis inhibiting action. The present inventors have made further studies and have completed the present invention.

Namely, the present invention relates to:

[1] a method of preparing a pharmaceutical composition comprising an enzyme-treated human serum, comprising a step of bringing a human serum into contact with β-galactosidase,

[2] the preparation method according to the above [1], further comprising a step of bringing the human serum into contact with sialidase,

[3] a pharmaceutical composition comprising an enzyme-treated human serum and being prepared by the preparation method according to the above [1] or [2],

[4] the pharmaceutical composition according to the above [3], wherein the human serum is prepared from a blood collected from a healthy another person,

[5] the pharmaceutical composition according to the above [3] or [4], wherein the pharmaceutical composition is used for a cancer or an infectious disease,

[6] the pharmaceutical composition according to the above [5], wherein the human serum is prepared from a blood collected from a patient suffering from a cancer or a patient suffering from an infectious disease and the pharmaceutical composition is administrated to the patient from whom the blood is collected,

[7] The pharmaceutical composition according to any one of the above [3] to [6], comprising proteins in an amount of from 0.1 mg/kg to 2.0 mg/kg for one dose.

It is preferable that the preparation method further comprises a step of bringing the human serum into contact with sialidase.

It is preferable that the human serum is prepared from a blood collected from a healthy another person.

It is preferable that the pharmaceutical composition is used for a cancer or an infectious disease.

It is preferable that the human serum is prepared from a blood collected from a patient suffering from a cancer or a patient suffering from an infectious disease.

It is preferable that the pharmaceutical composition is administrated to the patient from whom the blood is collected.

It is preferable that the pharmaceutical composition comprises proteins in an amount of from 0.1 mg/kg to 2.0 mg/kg for one dose.

Effect of the Invention

The pharmaceutical composition comprising an enzyme-treated human serum of the present invention has excellent macrophage activating action and/or angiogenesis inhibiting action, and therefore, is useful for treatment and prevention of diseases such as a cancer and an infectious disease, and can be used as an anticancer agent, an antiinfectious agent (antiviral agent) and the like. Further, the pharmaceutical composition can be used also as an inhibiting agent and a prophylactic agent for metastasis of a cancer since it has an angiogenesis inhibiting action.

Further, the pharmaceutical composition of the present invention can be prepared by using a serum of a patient, and in this case, a risk of an adverse effect attributable to an immunoresponse and a risk of infection of an unknown infectious disease, resulting from use of a blood serum of another person, can be eliminated.

Furthermore, since the enzyme-treated human serum in the present invention can be prepared by treating a human serum with β-galactosidase or β-galactosidase and sialidase, the method of preparing the pharmaceutical composition of the present invention comprising it has advantages such as easiness and low cost.

EMBODIMENT FOR CARRYING OUT THE INVENTION

Figure 1:
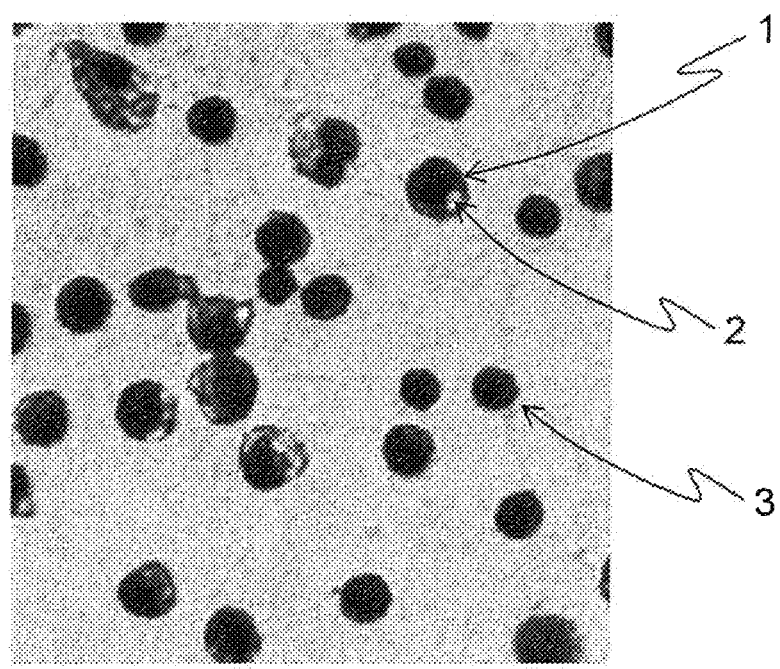
FIG. 1 is a photograph used in place of a drawing, which shows macrophages subjected to Giemsa-staining for evaluating phagocytic capability.

A serum to be used in the present invention is not limited particularly, and any of serums can be used as far as they are prepared from a blood collected from a human, and such serums can be prepared by a usual method. In consideration of a risk of an adverse effect attributable to an immunoresponse and a risk of infection of an unknown infectious disease that are resulting from use of a blood serum of another person, it is preferable that a serum is one prepared from a blood of a patient to whom the anticancer or antiinfectious pharmaceutical composition of the present invention is to be administrated. Otherwise, from the viewpoint of expectation of an advantageous effect by using, as a starting material, a blood which has not been subject to a baneful influence by a disease such as a cancer and/or an infectious disease, a serum prepared from a blood of a healthy another person is preferred. Herein, "a healthy another person" means a person who is other than a patient receiving treatment and is not suffering from a disease such as a cancer and/or an infectious disease.

β-Galactosidase to be used in the present invention is not limited particularly, and any kind of known β-galactosidases can be used. Examples are one derived from *Escherichia coli*, one derived from bovine liver, and the like. Examples of commercially available β-galactosidases are Catalogue No. 072-04141 of Wako Pure Chemical Industries, Ltd., G1875 of SIGMA-ALDRICH, and the like.

In the present invention, β-galactosidases can be used alone or can be used in combination of two or more thereof.

Sialidase to be used in the present invention is not limited particularly, and any kind of known sialidases can be used. Examples are one derived from *Clostridium perfringens*, one derived from *Streptococcus* 6646K, one derived from *Vibrio cholerae*, one derived from *Arthrobacter ureafaciens*, and the like. Examples of commercially available sialidases are Sigma product Nos. N2876, N2133, N2904, N3001 and N5631 of SIGMA-ALDRICH, Code No. 120052 of SEIKAGAKU BIOBUSINESS CORPORATION, Catalogue # P0720L and P0720S of BioLabs, and the like.

In the present invention, sialidases can be used alone or can be used in combination of two or more thereof.

In the present invention, it is preferable that the human serum is brought into contact with β-galactosidase or sialidase (enzyme treatment) by using a sufficient amount of enzyme for a sufficient period of time to such an extent that the enzyme reaction does not proceed substantially any more. For such a purpose, though an amount and time for the treatment depends on kind of an enzyme, for example, when Catalogue No. 072-04141 of Wako Pure Chemical Industries, Ltd. is used as β-galactosidase, it is enough to use the enzyme in an amount of 65 mU to 100 μl of a human serum. Further, for example, when the product No. N2876 of SIGMA-ALDRICH is used as sialidase, it is enough to use the enzyme in an amount of 65 mU to 100 μl of a human serum. In this case, it is sufficient to carry out the enzyme treatment for three hours.

The enzyme treatment can be carried out in a vessel of free choice by adding these enzymes into a human serum, and if desired, a buffering solution usually used in this field may be added thereto in order to adjust a total protein concentration in the human serum. Examples of such a buffering solution are saline solution, phosphate buffered saline (SPB), Ringer solution, and the like.

The enzyme treatment temperature is not limited particularly as far as the enzyme exhibits its activity, and is a temperature around 37° C. where the enzyme usually shows a high activity.

The enzyme treatment is terminated by heating (heat treatment), thereby inactivating the enzyme. Such heat treatment is not limited particularly as far as the enzyme can be inactivated, and for example, can be carried out by heating at a temperature around 60° C. for about 10 minutes.

The sample after the heat treatment may be subjected to condensing if desired. The condensing can be carried out by using commercially available equipment, for example, a centrifugal thickener (for example, 10000MWCO YM-10 of MILLIPORE CORPORATION).

The enzyme treatment can be carried out also by using an enzyme fixed to a solid phase (immobilized enzyme). A method of fixing the enzyme to a solid phase is known to a person ordinarily skilled in the art, and for example, β-galactosidase and/or sialidase can be fixed to agarose beads by using a silane coupling agent such as cyanogens bromide. Examples of such immobilized enzyme commercially available are immobilized β-galactosidase G3M (#A3102, MoBiTec), neuraminidase agarose derived from *Clostridium perfringens* (Welch *bacillus*) (Product No. N5254 available from SIGMA-ALDRICH), and the like. An advantage of use of an immobilized enzyme is such that an enzyme can be recovered without being inactivated by heat treatment after enzyme treatment, and as a result of such recovery, contaminants (proteins such as enzyme inactivated by heat treatment, and the like) can be decreased.

The thus obtained enzyme-treated human serum of the present invention can be used as a pharmaceutical composition as it is, and further, pharmaceutically acceptable carriers may be optionally blended thereto. Any of carriers used usually in this field can be used as such pharmaceutically acceptable carriers, and examples thereof are a diluent, a stabilizer, a preservative, a buffer agent, and the like.

The dosage form of the pharmaceutical composition of the present invention is not limited particularly, and an injection is preferable. The injection can be prepared by adding, according to necessity, a diluent, a stabilizer, a preservative, a buffer agent, and the like to the enzyme-treated human serum of the present invention. Examples of the administration form are intravenous injection, hypodermic injection, intradermic injection, intramuscular injection, intraperitoneal injection, and the like. Preferred is intramuscular injection.

The dose of the pharmaceutical composition of the present invention varies depending on age, sex, body weight and symptom of a patient, an administration route, and the like. A representative example of the dosage for one dose is such that a total amount of proteins contained in the pharmaceutical composition is within a range from about 0.1 mg to about 2.0 mg, preferably from about 0.2 mg to about 2.0 mg, further preferably from about 0.3 mg to about 1.3 mg, per 1 kg of body weight. Herein, the amount of protein is calculated from a protein concentration determined based on an absorbance at a wavelength of 570 nm.

With respect to the dosing interval and the number of doses, in case of dosing the pharmaceutical composition of the present invention with the above-mentioned dosage per one dose, the representative number of doses is 1 to 2 times per week and totally 12 to 24 times. The representative dosing interval is preferably two doses per week at an initial dosing stage (for example, 1 to 2 months) and thereafter, one dose per week. The dosage and the dosing interval may be optionally changed within a range where the total amount of a protein to be dosed is equal by using the total amount of proteins contained in the pharmaceutical composition as an index.

The pharmaceutical composition of the present invention has a macrophage activating action and/or an angiogenesis inhibiting action. Therefore, the pharmaceutical composition of the present invention can be used as a therapeutic agent or a prophylactic agent for diseases which can be cured or prevented by these actions. Examples of such diseases are cancers and infectious diseases.

Cancers include any of carcinomas, sarcomas and malignant tumors, for examples carcinoma cutaneum, bronchial carcinoma, lung cancer, non-small-cell lung cancer, mammary cancer, ovarium cancer, tongue cancer, pharyngeal cancer, esophageal carcinoma, gastric cancer, intestinum tenue cancer, intestinum crassum cancer, rectum cancer, colon cancer, hepatic cancer, pancreas cancer, renal cancer, renal cell carcinoma, vesical cancer, prostatic cancer, uterine cancer, cervical cancer, Wilms' tumor, melanotic carcinoma, meningioma, neuroblastoma, osteosarcoma, Kaposi sarcoma, lymphoma, leukaemia, and the like. In addition, herein, the term "cancer" includes these malignant tumors and metastases thereof.

Further, examples of infectious diseases are viral infectious diseases, for example, HIV infectious diseases, AIDS, and the like.

The pharmaceutical composition of the present invention can be used in combination with other anticancer agents and antiinfective agents In the case of combination use, the dosage of the pharmaceutical composition of the present invention is properly adjusted in consideration of indication, effect and dosage of the other medicaments.

The pharmaceutical composition of the present invention can be prepared by using a blood collected from a person other than a patient (for example, a healthy person) for administration to the patient, or also, can be prepared by using a blood collected from a patient himself for administration to him. In the former case where a blood is collected from a healthy person, an advantageous effect can be expected by using a blood which has not been subject to a baneful influence by a disease such as a cancer or an infectious disease. Meanwhile, in the latter case, a risk of an adverse effect attributable to an immunoresponse and a risk of infection of an unknown infectious disease, resulting from use of a blood of another person, can be eliminated.

EXAMPLE

The present invention is then explained by means of Examples, but is not limited thereto.
Preparation of enzyme-treated human serum
(Sample 1)

From a patient (generic character: male, 63-year old, familial hypercholesterolemia), 50 ml of blood was collected in a vacuum blood collecting tube. The blood was subjected to centrifuging (3000 rpm, 10 minutes) to separate hemocyte components and obtain a serum.

Out of the obtained serum, 100 µl was put in an Eppendorf tube, and thereto were added 6.5 µl of β-galactosidase (Catalogue No. 072-04141 available from Wako Pure Chemical Industries, Ltd., 10 mU/µl), 6.5 µl of sialidase (N2876 available from SIGMA-ALDRICH, 10 mU/µl), and 87 µl of 100 mM SPB (15.601 g of $NaH_2PO_4.2H_2O$ and 35.814 g of $Na_2HPO_4.12H_2O$ were dissolved in 500 ml of distilled water to prepare 200 mM SPB (pH 7.0), followed by dilution to 100 mM SPB), followed by 3-hour incubation at 37° C. After the incubation, 200 µl of 100 mM SPB was further added, followed by 10-minute heat treatment at 60° C. and then condensing with MICROCON (10000MWCO YM-10 of MILLIPORE). A protein concentration determined by an absorbance determination at a wavelength of 570 nm (using a calibration curve of BSA (bovine serum albumin, SIGMA, A4503)) was 79.4 µg/µl (Sample 1).

This Sample 1 was diluted by using 100 mM SPB to prepare each of (Sample 1-1), (Sample 1-2), (Sample 1-3), (Sample 1-4), (Sample 1-5) and (Sample 1-6) having a protein concentration of 0.1 ng/10 µl, 1 ng/10 µl, 10 ng/10 µl, 100 ng/10 µl, 1 µg/10 µl and 10 µg/10 µl, respectively.

In addition, Sample 1 was diluted by using a saline solution containing 1% methyl cellulose (here, a saline solution means a 0.9% NaCl solution) to prepare each of (Sample 1-7), (Sample 1-8), (Sample 1-9) and (Sample 1-10) having a protein concentration of 0.1 ng/10 µl, 1 ng/10 ng/10 µl and 100 ng/10 respectively.
(Sample 2)

From a patient (generic character: male, 63-year old, familial hypercholesterolemia), a blood was collected and treated in the same manner as in the preparation of Sample 1 to obtain Sample 2 (protein concentration: 137.96 µg/µl).
(Comparative Sample 1)

With respect to the serum before the enzyme treatment in the preparation of Sample 1, the protein concentration thereof determined in the same manner as above was 134.1 µg/µl (Comparative Sample 1). The Comparative Sample 1 was diluted by using 100 mM SPB to prepare each of (Comparative Sample 1-1), (Comparative Sample 1-2), (Comparative Sample 1-3), (Comparative Sample 1-4), (Comparative Sample 1-5) and (Comparative Sample 1-6) having a protein concentration of 0.1 ng/10 µl, 1 ng/10 µl, 10 ng/10 µl, 100 ng/10 µl, 1 µg/10 µl and 10 µg/10 µl, respectively.

In addition, the Comparative Sample 1 was diluted by using a saline solution containing 1% methyl cellulose to prepare each of (Comparative Sample 1-7), (Comparative Sample 1-8), (Comparative Sample 1-9) and (Comparative Sample 1-10) having a protein concentration of 0.1 ng/10 µl, 1 ng/10 µl, 10 ng/10 µl and 100 ng/10 µl, respectively.
(Comparative Sample 2)

Further, TX-1934 (2-[(4-methoxy-3,5-dimethylphenyl)methylene]-4-cyclopentene-1,3-dione) was dissolved in a mixed solvent of DMSO, saline solution and saline solution containing 2% methyl cellulose in a mixing ratio of 1:9:10 to obtain Comparative Sample 2 having a concentration of 10

µg/10 µl. Comparative Sample 2 was used as a positive control in the observation of an angiogenesis inhibiting action.

2. Phagocytotic Activity of Macrophage

A mouse (8-week old, ICR female mouse, Japan SLC, Inc.) was made to suffer from cervical dislocation, an integument of its abdomen was peeled off, and 10 ml of phosphate buffered saline (PBS containing 0.01 M of sodium phosphate, 0.9% NaCl and 5 units/ml of heparin) was injected in its abdominal cavity without injuring viscera. After tapping of the abdomen for about one minute, an intra-abdominal liquid was recovered to collect peritoneal cells. After subjecting the intra-abdominal liquid to centrifuging (1000 rpm, 4° C., 15 minutes), a supernatant was disposed, and an RPMI culture medium was added, followed by pipetting. The number of cells was measured with a Burker-Turk hemacytometer, and an RPMI culture medium was further added to adjust the number of cells to be $1.0 \times 10^6$ cells/ml. The RPMI culture medium was prepared in such a manner as mentioned below. Namely, after dissolving a powder culture medium (Catalogue No. 856846 available from GIBCO) in 900 ml of purified water, further, 2 g of $NaHCO_3$ was dissolved thereinto in a clean bench. After adjusting a pH value of the mixture to be 7.2 with 1NHCl, the total amount of the mixture was adjusted to be 1000 ml with purified water. The thus obtained solution was subjected to filtering with a filter (SLGVJ13SL of MILLIPORE) to obtain an RPMI culture medium which was then stored at 4° C. before the use.

The macrophage solution obtained above was dispensed in each of wells on a plate with 24 wells (TPP, 92024) in an amount of 500 µl/well ($5.0 \times 10^5$ cells/well), in which three sterilized cover glasses (Micro cover glass No. 1 of Matsunami Glass Ind., Ltd.) were put in each of wells. Further, an RPMI culture medium was added in an amount of 500 µl/well to be totally 1 ml/well. After subjecting the plate to 1-hour incubation at 37° C., the solutions in each of the wells were disposed, and each well was washed with 1 ml of RPMI culture medium twice. After the washing, 1 ml of an RPMI culture medium was added in each of wells, followed by 15-hour incubation at 37° C.

After the incubation, 10 µl each of Samples 1-1 to 1-6 and Comparative Samples 1-1 to 1-6 prepared above was added in each well, followed by 3-hour incubation at 37° C. to stimulate the macrophages. After the incubation, the solutions of each well were disposed, and 1 ml of 0.5% opsonized SRBC (sheep red blood cells of Nippon Bio-Supp. Center) was added, followed by 90-minute incubation at 37° C. to make the macrophages phagocytose the SRBC. After the phagocytosis, the cover glasses were washed with ⅕×PBS, 1×PBS and 1×PBS in order, followed by air drying for about 30 minutes. After the air drying, each cover glass was dipped in methanol (25183-2B of KANTO CHEMICAL CO., INC.) for about one minute to fix methanol to the cover glass. After the fixing, the cover glass was subjected to about 30-minute air drying again and then staining with a Giemsa solution (A1327 of SIGMA) diluted 20 times with PBS was conducted for one hour. After the staining, the cover glass was washed with tap water from its back surface and air-dried overnight.

After the air drying, the back surface of the cover glass was stuck to a slide glass (micro slide glass 52215 of Matsunami Glass Ind., Ltd.). Photographs were taken at 9 points per one cover glass with a light microscope (ECLIPSE E200 of Nikon Corporation). The number of macrophages, the number of phagocytosed SRBCs and the number of phagocytosing macrophages which were observed totally were counted and the respective total numbers at 9 points were summed up. An ingestion index was calculated by multiplying a ratio of macrophages having phagocytosed SBRC to the total macrophages counted by an average number of ingestions of one macrophage. FIG. 1 is a photograph after the Giemsa staining. By the Giemsa staining, macrophages are observed as purple spheres and SRBCs are observed as transparent spheres. The ingestion index was calculated based on the condition that SRBCs being in contact with macrophages were deemed as phagocytosed SRBCs and macrophages being in contact with SRBCs were deemed as phagocytosing macrophages.

For each of samples, three ingestion indices were calculated in the respective cover glasses, and an average thereof was obtained. With respect to a control, RPMI culture media was used instead of the samples or comparative samples, and operations therefor were carried out in the same manner as above.

Figure 2:
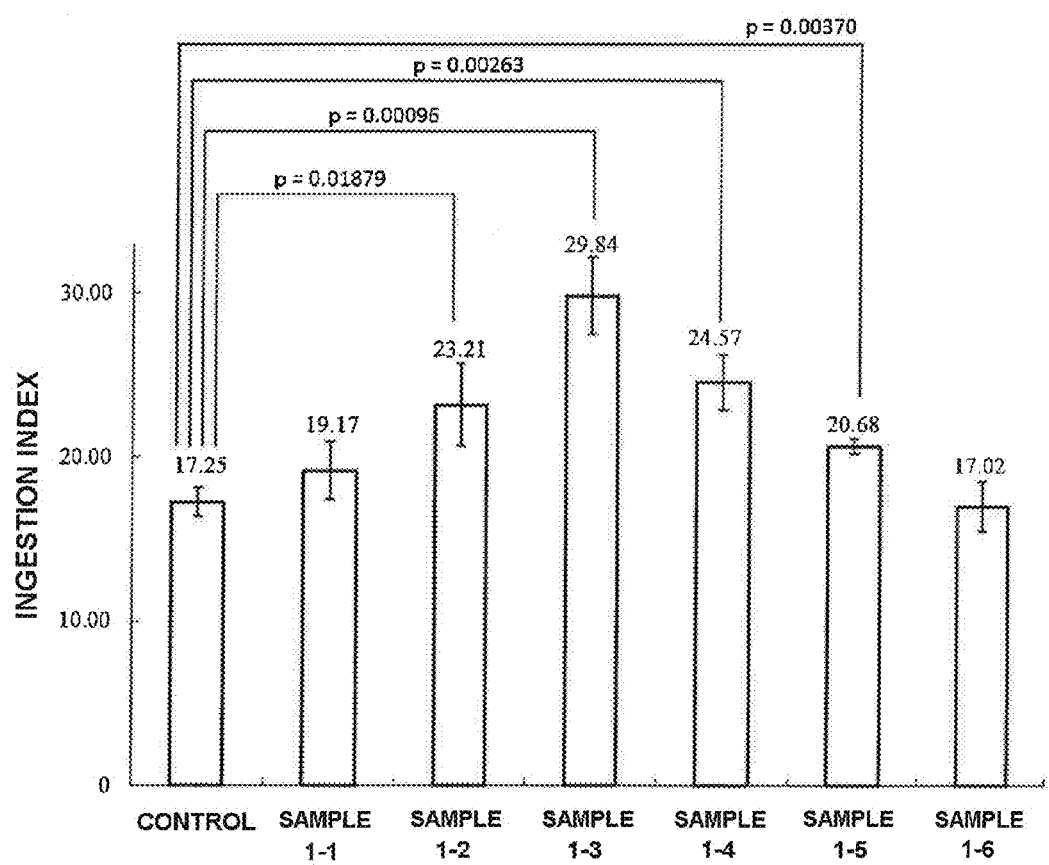
FIG. 2 is a graph showing the results of phagocytic activity of macrophages by using 0.5% opsonized SRBC with respect to samples of the present invention.
Figure 3:
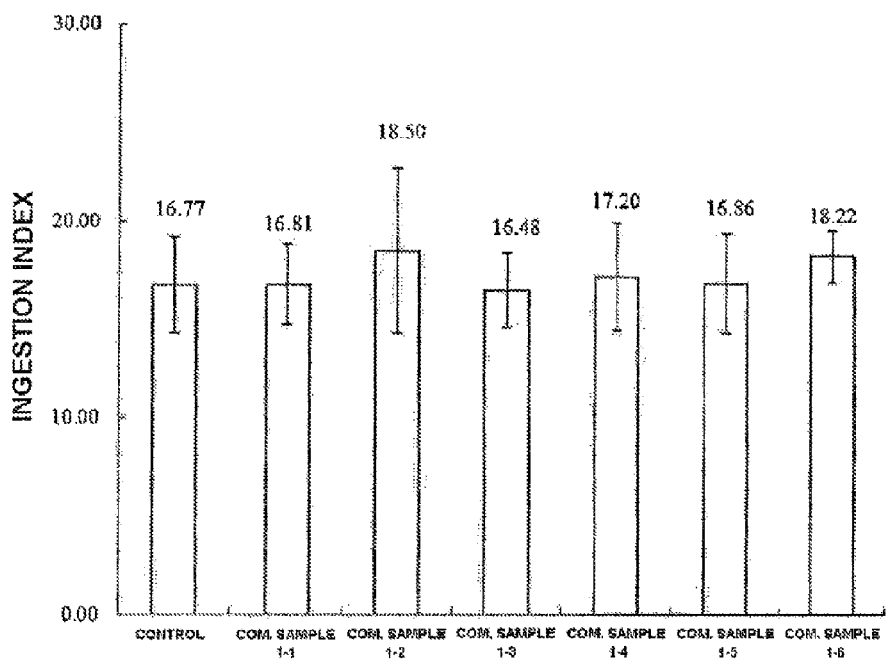
FIG. 3 is a graph showing the results of phagocytic activity of macrophages by using 0.5% opsonized SRBC with respect to comparative samples.

The results are shown in Tables 1 and 2 (Phagocytotic activity of intra-abdominal mouse macrophage by using opsonized SRBC) and FIGS. 2 and 3.

TABLE 1

|  | Amount of protein (ng) | Ingestion index (average value) | Standard deviation |
|---|---|---|---|
| Control | 0 | 17.25 | 0.87 |
| Sample 1-1 | 0.1 | 19.17 | 1.76 |
| Sample 1-2 | 1.0 | 23.21 | 2.56 |
| Sample 1-3 | 10 | 29.84 | 2.35 |
| Sample 1-4 | 100 | 24.57 | 1.69 |
| Sample 1-5 | 1000 | 20.68 | 0.44 |
| Sample 1-6 | 10000 | 17.02 | 1.52 |

TABLE 2

|  | Amount of protein (ng) | Ingestion index (average value) | Standard deviation |
|---|---|---|---|
| Control | 0 | 16.77 | 2.44 |
| Com. Sample 1-1 | 0.1 | 16.81 | 2.03 |
| Com. Sample 1-2 | 1.0 | 18.50 | 4.21 |
| Com. Sample 1-3 | 10 | 16.48 | 1.89 |
| Com. Sample 1-4 | 100 | 17.20 | 2.76 |
| Com. Sample 1-5 | 1000 | 16.86 | 2.55 |
| Com. Sample 1-6 | 10000 | 18.22 | 1.34 |

3. Angiogenesis Inhibiting Action (Chorioallantois (CAM) Assay)

(Day 1) Pre-Incubation

A hen's fertilized egg for the first incubation (Day 0) was placed on an egg stand with its sharp end facing downward and was left in an incubator for four days at 37.6° C. for pre-incubation. A vat filled with SDW (sterilized water) was placed at the bottom inside of the incubator to keep the humidity.

(Day 5) Preparation for Addition of a Reagent (Enzyme-Treated Human Serum)

Figure 4A:
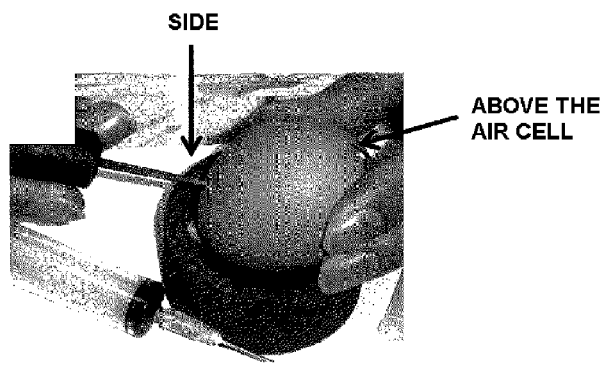
FIG. 4(A) is a photograph used in place of a drawing, which shows a fertilized egg with holes bored by using a gimlet at two points of an egg shell, i.e., a point above an air cell and a point at a side of an egg.
Figure 4B:
FIG. 4(B) is a photograph used in place of a drawing, which shows a fertilized egg in a state of a part of its shell membrane being removed by using a pair of forceps with sharp ends.

The fertilized egg subjected to 4-day pre-incubation was taken out of the incubator as being placed on the egg stand, and after disinfection of the fertilized egg with cotton impregnated with 70% ethanol, holes were bored with a gimlet at two points of an egg shell, i.e. a point above an air cell and a point at a side of the egg (FIG. 4(A)). About 4 ml of egg white was sucked and removed from the hole at the side of the egg with an injection syringe (10 ml, 18 G) while a pinhole of the needle of the syringe was oriented toward the egg shell. Next, a silicon dropping pipet was fit to the hole above the air cell, and yolk sac and lecithoblast were separated from the shell membrane by sucking. The hole at the side of the egg was sealed with Tegaderm. The sealed fertilized egg was transferred to a clean bench, and the egg shell around the hole above the air cell was removed with a pair of forceps having bent edges to widen the hole to about 1 cm in a diameter and expose the shell membrane. A part of the exposed shell membrane was removed with a pair of forceps having pointed ends (FIG. 4(B)). A stainless steel cap is put over the air cell, followed by 24-hour incubation in an incubator kept at 39° C. under a given humid.

(Day 6) Addition of a Reagent

The fertilized egg was taken out of the incubator and transferred to a clean bench. The stainless steel cap was removed, and CAM was classified into three sizes (1: 5 mm or more of diameter, 2: more than 3 mm and less than 5 mm of diameter, 3: less than 3 mm of diameter). CAM was classified such that the size of CAM was nearly equal to each other in each of groups to which different samples are added, and each of CAM was arranged with labels being stuck thereto to identify which sample is added thereto. In this case, most grown CAM was selected for a group of controls.

Figure 5:
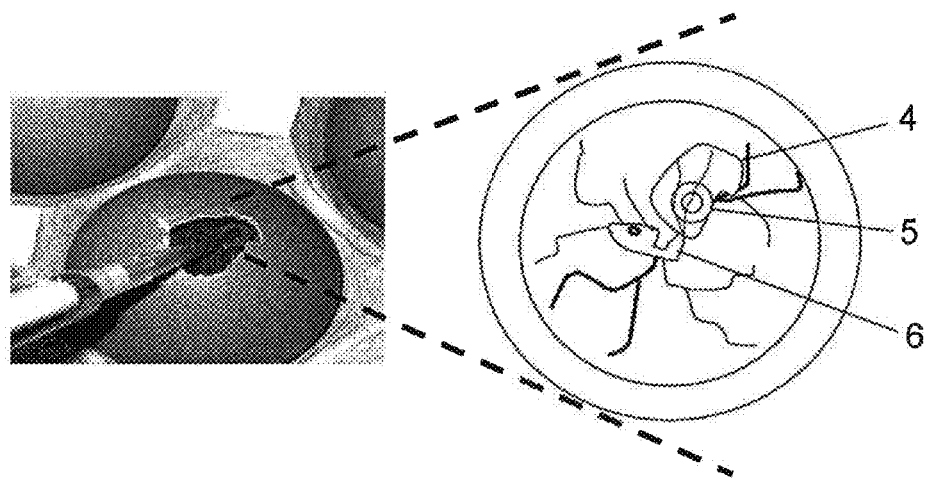
FIG. 5 is a photograph used in place of a drawing, which shows a state of each sample being dosed to a fertilized egg.

A silicon ring was put nearly on a center of CAM, and 10 μl of each sample was added in the center of the silicon ring (FIG. 5). In addition, for the control, 10 μl of a solvent prepared by mixing DMSO, saline solution and saline solution containing 2% methyl cellulose in a ratio of 1:9:10 was added. The stainless steel cap was again put on the egg, and the egg was returned to the incubator.

(Day 7) Check of Ring Position

The fertilized egg was taken out of the incubator and transferred to a clean bench. The stainless steel cap was removed to check to see that the ring was placed on CAM. If the ring has been moved, it was slid onto CAM with a pair of forceps having pointed ends. After that, the stainless steel cap was again put on the egg, and the egg was returned to the incubator. The incubator temperature was changed to 39.5° C. and the incubation was continued.

(Day 8) Judgment

The fertilized egg was taken out of the incubator and placed on a laboratory testing bench. The egg shell was removed with a pair of scissors to widen the hole so as to make observation of CAM easy. In this case, when a shell membrane had been left un-removed, it was peeled away with a pair of forceps having pointed ends not to injure a blood vessel. About 1 ml of Intralipos injection (Approval No. 22000AMX00284 available from OTSUKA PHARMACEUTICAL CO., LTD.) was taken in a syringe (1 ml, 27 G), and the syringe was injected into a portion of CAM where the number of blood vessels is small to slowly inject Intralipos injection with attention not to cause air to enter thereinto. In this case, when leakage of the Intralipos or shedding of blood occurred, it was wiped off with Kimwipe.

An angiogenesis inhibiting effect of each egg was judged according to the criteria shown in Table 3.

TABLE 3

| Criteria for judging an angiogenesis inhibiting effect | | |
|---|---|---|
| Judgment | Point | Evaluation |
| − | 0 | No angiogenesis inhibition is found. |
| ± | 1 | Whether or not there is angiogenesis inhibition cannot be judged. |
| + | 2 | Inhibited portion is partly found in a blood capillary on CAM. |
| ++ | 3 | Angiogenesis in a blood capillary on CAM is completely inhibited. |
| +++ | 4 | There is angiogenesis inhibition on a thick vessel. |

Points of each sample were calculated based on the points obtained in each egg by the equation (1):

$$\text{Point of sample compound} = \frac{\left\{\begin{array}{l}(\text{Number of eggs of} \pm \times 1) + \\ (\text{Number of eggs of} + \times 2) + \\ (\text{Number of eggs of} ++ \times 3) + \\ (\text{Number of eggs of} +++ \times 4)\end{array}\right\}}{\text{Total number of eggs}} \quad \text{Equation (1)}$$

and based on the thus obtained points of each sample, an angiogenesis inhibition index was calculated by the equation (2):

$$\text{Angiogenesis inhibition index} = \frac{\text{Point of sample compound}}{\text{Point of control}} \quad \text{Equation (2)}$$

and an angiogenesis inhibiting action was evaluated. The results are shown in Tables 4 and 5.

TABLE 4

| | Protein concentration (ng/CAM) | Point of each sample | Angiogenesis inhibition index |
|---|---|---|---|
| Control | 0 | 0.92 | 1.00 |
| Com. Sample 2 (positive control) | 10 | 1.67 | 1.82 |
| Sample 1-7 | 0.1 | 1.00 | 1.09 |
| Sample 1-8 | 1.0 | 1.18 | 1.29 |
| Sample 1-9 | 10 | 1.08 | 1.18 |
| Sample 1-10 | 100 | 1.50 | 1.64 |

TABLE 5

| | Protein concentration (ng/CAM) | Point of each sample | Angiogenesis inhibition index |
|---|---|---|---|
| Control | 0 | 0.83 | 1.00 |
| Com. Sample 2 (positive control) | 10 | 1.27 | 1.53 |
| Com. Sample 1-7 | 0.1 | 0.50 | 0.60 |
| Com. Sample 1-8 | 1.0 | 0.42 | 0.50 |
| Com. Sample 1-9 | 10 | 0.77 | 0.92 |
| Com. Sample 1-10 | 100 | 0.60 | 0.72 |

4. Antitumor Activity (Ehrlich Ascites Carcinoma Carrying Mouse)

Ehrlich ascites carcinoma cells (obtained by culturing in vivo from cytopoiesis up to 2nd passage) were implanted in an abdominal cavity of a group of five ICR mice (10-week old, female) ($1 \times 10^7$ cells/mouse). A saline solution containing Sample 2 was administrated in an abdominal cavity of each mouse in an amount of 0.1 ml/mouse once per day for seven days from the next day of the implantation. The dosage of Sample 2 was adjusted such that the total amount of dosed protein reached 11.25 μl/kg in each of mice. The saline solution containing Sample 2 for 7 administrations was prepared in one lot, was passed through a 0.22 μm sterilized filter and was kept at 4° C. under light-shielded condition before the use. As for the control, a saline solution was administrated in an equivalent amount (0.1 ml/mouse) instead of a saline solution containing Sample 2.

After the implantation of carcinoma cells, a change in a body weight of a mouse was observed over 15 days (a period of time in which neither decease nor dropping off occurred in any group of mice), and thereafter, whether the mice were live or dead was checked succeedingly. The results are shown in Table 6 and FIG. 6 (The body weight was an average of a group of mice. The bars represent standard deviations.).

TABLE 6

| | | Days after implantation of carcinoma cells | | | | | | | | | | | |
|---|---|---|---|---|---|---|---|---|---|---|---|---|---|
| | | 15 | 16 | 17 | 18 | 19 | 20 | 21 | 22 | 23 | 24 | 25 | 26 | 27 |
| Survival ratio (%) | Group of mice dosed with Sample 2 | 100 | 100 | 100 | 100 | 100* | 100 | 100 | 100 | 75 | 25 | 25 | 25 | 0 |
| | Group of controls | 100 | 80 | 20 | 20 | 20 | 20 | 20 | 0 | — | — | — | — | — |

*One mouse died by fighting (excluded in the calculation of the survival ratio).

With respect to the above results, a significant difference assay was carried out by Log-rank (Mantel-Cox) test and Gehan-Breslow-Wilcoxon test by using Prism 5.04 (version for demonstration) of GraphPad Software, and the result of the assay indicated that the survival ratio of the group of mice dosed with Sample 2 was significantly higher than that of the group of controls (P<0.01).

Figure 6:
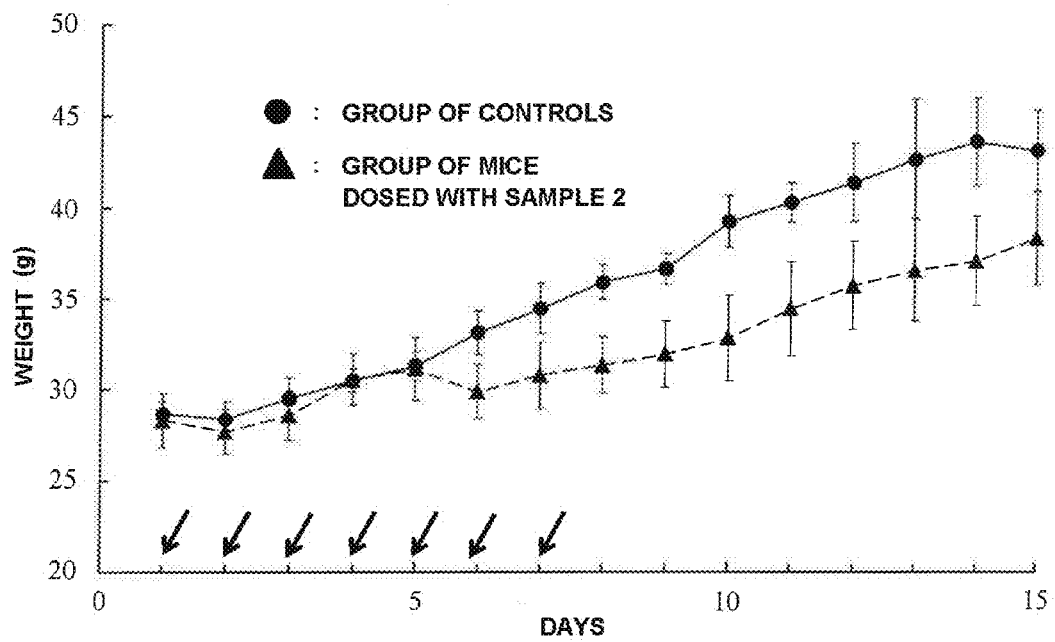
FIG. 6 is a graph showing a change of a weight of mice in an antitumor activity test by using mice having Ehrlich ascites carcinoma (a change of a weight after transplantation of the cancer cells).

Further, from the results of FIG. 6, it is seen that an increase in weight is inhibited in the group of mice dosed with Sample 2 as compared with the group of controls. This is because the growth of Ehrlich ascites carcinoma cells was inhibited in the group of mice dosed with the samples.

INDUSTRIAL APPLICABILITY

The pharmaceutical composition comprising an enzyme-treated human serum of the present invention has excellent macrophage activating action and/or angiogenesis inhibiting action, and therefore is useful as a therapeutic agent and a prophylactic agent for diseases such as a cancer and an infectious disease and as a inhibiting agent and a prophylactic agent for metastasis of a cancer.

Explanation of Symbols
1: Phagocytosing macrophage
2: Phagocytosed SRBC
3: Macrophage
4: Chorioallantois (CAM)
5: Silicon ring
6: Embryo

The invention claimed is:

1. A method of treating a human suffering from cancer, consisting essentially of:
    administering a therapeutically effective amount of a pharmaceutical composition consisting essentially of a beta-galactosidase and sialidase treated human serum to the human suffering from cancer,
    said composition being prepared by bringing a human serum from blood of a healthy human into contact with beta-galactosidase and sialidase to yield the pharmaceutical composition;
    wherein the pharmaceutical composition consists essentially of proteins in an amount of 0.1 mg/kg to 2.0 mg/kg per dose; and
    wherein the cancer is selected from the group consisting of uterine cancer, prostatic cancer, lymphoma, and intestinum crassum cancer.

* * * * *